(12) United States Patent
Kaneko

(10) Patent No.: US 6,492,342 B1
(45) Date of Patent: Dec. 10, 2002

(54) HYGROMYCIN A PRODRUGS

(75) Inventor: Takushi Kaneko, Guilford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/698,399

(22) Filed: Oct. 27, 2000

Related U.S. Application Data

(60) Provisional application No. 60/162,722, filed on Oct. 29, 1999.

(51) Int. Cl.[7] .............................................. A01N 43/04
(52) U.S. Cl. ........................ 514/35; 514/25; 536/16.8; 536/17.9; 536/18.1
(58) Field of Search .............................. 536/16.8, 17.9, 536/16.1; 514/35, 25

(56) References Cited

U.S. PATENT DOCUMENTS 6,245,745 B1 * 6/2001 Hayward ..................... 519/25

OTHER PUBLICATIONS

Jaynes, B.H. et al., "Synthesis and In Vitro Antibacterial Activity of Hygromycin A Analogs Modified at the C4' Aryl Position," Bioorganic & Medicinal Chemistry Letters, vol. 3 No. 8, pp. 1531–1536 (1993).

* cited by examiner

Primary Examiner—Elli Peselev
(74) Attorney, Agent, or Firm—Peter C. Richardson; Gregg C. Benson; Jeffrey N. Myers

(57) ABSTRACT

This invention relates to compounds of the formula

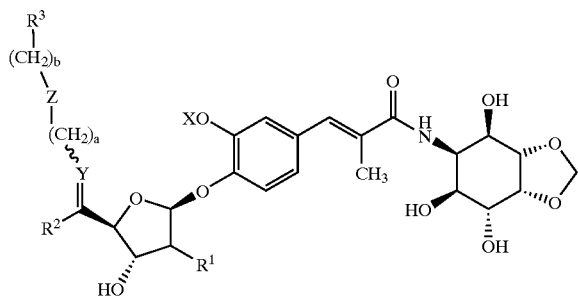

and to pharmaceutically acceptable salts and solvates thereof, wherein a, b, X, Y, Z, $R^1$, $R^2$, and $R^3$ are as defined herein. The compounds of formula I are antibacterial and antiprotozoal agents useful for treating various bacterial and protozoal infections and disorders related to such infections. The invention also relates to pharmaceutical compositions containing the compounds of formula I, to methods of treating bacterial and protozoal infections by administering the compounds of formula I, and to methods for preparing compounds of formula I.

16 Claims, No Drawings

HYGROMYCIN A PRODRUGS

CROSS REFERENCE TO RELATED APPLICATIONS

This application claims the bendfit of U.S. Provisional. Application No. 60/162,722, filed Oct. 29, 1999.

BACKGROUND OF THE INVENTION

This invention relates to novel hygromycin A prodrugs that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment. The hygromycin prodrugs of this invention possess an advantage over the parent drugs in terms of efficacy, formulation, solubility, side effects or stability.

Hygromycin A is a fermentation-derived natural product first isolated from *Streptomyces hygroscopicus* in 1953. As an antibiotic, hygromycin A possesses activity against human pathogens and is reported to possess potent in vitro activity against *Serpulina* (*Treponema*) *hyodysenteriae* which causes swine dysentery. Several references refer to semisynthetic modifications of hygromycin A, including the following: derivatization of the 5" ketone of hygromycin A to the 2,4-dinitrophenylhydrazone is referred to in K. Isono et al., *J. Antibiotics* 1957, 10, 21, and R. L. Mann and D. O. Woolf, *J. Amer Chem. Soc.* 1957, 79, 120. K. Isono et al., ibid., also refer to the thiosemicarbazone at 5"; reduction of the 5" ketone of hygromycin A to the 5" alcohol is referred to in R. L. Mann and D. O. Woolf, ibid., as well as in S. J. Hecker et al., *Bioorg. Med. Chem. Lett.* 1992, 2, 533 and S. J. Hecker et al., *Bioorg. Med. Chem. Lett.* 1993, 3, 295; furanose analogues are referred to in B. H. Jaynes et al., *Bioorg. Med. Chem. Lett.* 1993, 3, 1531, and B. H. Jaynes et al., *J. Antibiot.* 1992, 45, 1705; aromatic ring analogues are referred to in S. J. Hecker et al., *Bioorg. Med. Chem. Lett.* 1993, 3, 289, and C. B. Cooper et al., *Bioorg. Med. Chem. Lett.* 1997, 7, 1747; enamide analogues are referred to in S. J. Hecker et al., *Bioorg. Med. Chem. Lett.* 1992, 2, 533; aminocyclitol analogues are referred to in S. J. Hecker et al., *Bioorg. Med. Chem. Lett.* 1992, 2, 1015, and in S. J. Hecker et al., *Bioorg. Med. Chem. Lett.* 1992, 2, 1043. The hygromycin A derivatives of the present invention possess activity against both gram-negative and gram-positive bacteria and protozoa.

SUMMARY OF THE INVENTION

The present invention relates to compounds of the formula

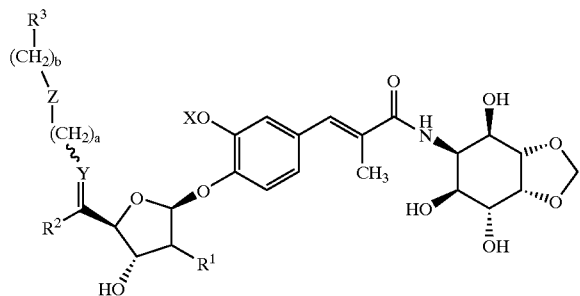

I or the pharmaceutically acceptable salts thereof; wherein a is 0 or 1;

b is 0, 1, 2 or 3;

$R^1$ is hydrogen or hydroxy;

$R^2$ is methyl;

$R^3$ is $(C_6-C_{10})$aryl optionally substituted by one to three groups independently selected from hydrogen, halo, $(C_1-C_6)$alkoxy, amino, $(C_1-C_6)$alkylamino, $((C_1-C_6)$alkyl$)_2$amino, nitro, $(C_1-C_6)$alkoxy, $(C_1-C_6)$alkoxyC(O), $(C_1-C_6)$alkylaminoC(O), $(C_6-C_{10})$aryl, $(C_2-C_9)$heterocycloalkyl, $(C_2-C_9)$heteroaryl or $(C_1-C_6)$alkyl optionally substituted by one to three fluoro;

X is $(R^4O)_2P(O)$—, $(R^4O)S(O)_n$—, $(C_6-C_{10})$arylC(O), $(C_2-C_9)$heteroarylC(O), $(C_2-C_9)$heterocycloalkylC(O), $(R^7)_2N(CHR^5)C(O)$—, $R^6$pyridinium$(C_1-C_6)$acyl, $(R^8)_3N^+(C_1-C_1-C_6)$acyl, $(C_1-C_6)$acyl, $(C_6-C_{10})$aryl$(C_1-C_3)$acyl, $(C_2-C_9)$heteroaryl$(C_1-C_3)$acyl and $(C_2-C_9)$heterocycloalkyl$(C_1-C_3)$acyl;

wherein n is 1 or 2;

$R^4$ is hydrogen, $(C_1-C_5)$alkyl, $(C_6-C_{10})$aryl or an alkaline metal;

$R^5$ is hydrogen, $(C_1-C_6)$alkyl optionally substituted by hydroxy, aminoC(O)—, thio, methylthio, carboxy or amino; $(C_6-C_{10})$aryl optionally substituted by hydroxy; or $(C_2-C_9)$heteroaryl;

$R^6$ is hydrogen, halo, nitro, amino, $(C_1-C_6)$alkylamino, $((C_1-C_6)$alkyl$)_2$amino, hydroxy, $(C_1-C_6)$alkoxy, $(C_1-C_6)$alkyoxyC(O) or $(C_1-C_6)$alkylaminoC(O);

$R^7$ is hydrogen, $(C_1-C_6)$alkyl, $(C_6-C_{10})$aryl or $(C_6-C_{10})$aryl$(C_1-C_6)$alkyl;

$R^8$ is hydrogen or $(C_1-C_6)$alkyl;

Y is CH or N, wherein the wavy bond symbol linking Y and $(CH_2)_a$ designates a single bond in either the "Z" or "E" configuration relative to the furanyl ring;

Z is oxygen or $NR^{12}$ wherein $R^{12}$ is hydrogen, $(C_1-C_6)$alkyl or $(C_6-C_{10})$aryl;

with the proviso that when Y is CH, a is 1; and with the proviso that when Y is nitrogen, a is zero.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties. Said alkyl group may include one or two double or triple bonds. It is understood that for said alkyl group to include a carbon—carbon double or triple bond at least two carbon atoms are required in said alkyl group.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, and also benzyl.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$heterocycloalkyl rings is through a carbon or a $sp^3$ hybridized nitrogen heteroatom.

($C_2$–$C_9$)Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidinyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyridinyl, benzo[b]thiophenyl, 5, 6, 7, 8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said ($C_2$–$C_9$)heterocycloalkyl rings is through a carbon atom or a $sp^3$ hybridized nitrogen heteroatom.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

Preferred compounds of formula I include those wherein Y is nitrogen, a is zero, Z is oxygen and b is 1. In an embodiment, the preferred compounds include those wherein $R^1$ is hydroxy, X is $(R^4O)_2P(O)$— and $R^4$ is hydrogen or alkaline metal. In another embodiment, the preferred compounds include those wherein $R^1$ is hydrogen, X is $(R^4O)_2P(O)$— and $R^4$ is hydrogen or alkaline metal. In another embodiment, the preferred compounds include those wherein $R^1$ is hydroxy and X is $(R^4O)S(O)_n$—, wherein n is 2 and $R^4$ is hydrogen or alkaline metal. In another embodiment, the preferred compounds include those wherein $R^1$ is hydrogen and X is $(R^4O)S(O)_n$—, wherein n is 2 and $R^4$ is hydrogen or alkaline metal. In another embodiment, the preferred compounds include those wherein $R^1$ is hydroxy and X is $R^6$pyridinium($C_1$–$C_3$)acyl, wherein n is 2 and $R^4$ is hydrogen or alkaline metal. In another embodiment, the preferred compounds include those wherein $R^1$ is hydrogen and X is $R^6$pyridinium($C_1$–$C_3$)acyl, wherein n is 2 and $R^4$ is hydrogen or alkaline metal.

Other preferred compounds of formula I include those wherein Y is CH, a is 1, Z is oxygen and b is zero. In an embodiment, the preferred compounds include those wherein $R^1$ is hydroxy, X is $(R^4O)_2P(O)$— and $R^4$, is hydrogen or formula alkaline metal. In another embodiment, the preferred compounds include those wherein $R^1$ is hydrogen, X is $(R^4O)_2P(O)$— and $R^4$ is hydrogen or alkaline metal.

Other preferred compounds of formula I include those wherein Y is CH, a is 1, Z is oxygen, b is zero and X is $R^6$pyridinium($C_1$–$C_3$)acyl or $(R^4O)S(O)_n$—, wherein n is 2 and $R^4$ is hydrogen or alkaline metal. In an embodiment thereof, $R^1$ is hydroxy. In another embodiment thereof, $R^1$ is hydrogen.

Other preferred compounds of formula I include those wherein Y is nitrogen, a is zero, Z is oxygen, b is 1, $R^1$ is hydroxy and X is $(R^4O)S(O)_n$— wherein n is 2 and $R^4$ is hydrogen or alkaline metal.

Other preferred compounds of formula I include those wherein Y is CH; a is 1, Z is oxygen, b is zero, $R^1$ is hydroxy and X is $(R^4O)_2P(O)$— wherein $R^4$ is hydrogen or alkaline metal.

Other preferred compounds of formula I include those wherein Y is nitrogen, a is zero, Z is oxygen, b is 1, $R^1$ is hydrogen and X is $(R^4O)_2P(O)$— wherein $R^4$ is hydrogen or alkaline metal.

Other preferred compounds of formula I include those wherein Y is nitrogen, a is zero, Z is oxygen, b is 1, $R^1$ is hydrogen and X is $(R^4O)S(O)_n$— wherein n is 2 and $R^4$ is hydrogen or alkaline metal.

Other preferred compounds of formula I include those wherein Y is CH; a is 1, Z is oxygen, b is zero, $R^1$ is hydroxy and X is $(R^4O)_2P(O)$— wherein $R^4$ is hydrogen or alkaline metal.

Other preferred compounds of formula I include those wherein Y is nitrogen, a is zero, Z is oxygen, b is 1, $R^1$ is hydroxy and X is $R^6$pyridinium($C_1$–$C_3$)acyl.

Other preferred compounds of formula I include those wherein Y is nitrogen, a is zero, Z is oxygen, b is 1, $R^1$ is hydrogen and X is $R^6$pyridinium($C_1$–$C_3$)acyl.

Other preferred compounds of formula I include those wherein Y is CH; a is 1, Z is oxygen, b is zero, $R^1$ is hydroxy and X is $R^6$pyridinium($C_1$–$C_3$)acyl.

Other preferred compounds of formula I include those wherein Y is nitrogen, a is zero, Z is oxygen, b is 1, $R^1$ is hydrogen and X is $R^6$pyridinium($C_1$–$C_3$)acyl.

Other preferred compounds of formula I include those wherein Y is CH; a is 1, Z is oxygen, b is zero, $R^1$ is hydroxy and X is $R^6$pyridinium($C_1$–$C_3$)acyl.

Specific preferred compounds of formula I including the following:

Phosphoric acid mono-(2-(5-(1-(3-chloro-benzyloxy-Z-imino)-ethyl)-3,4-dihydroxy-tetrahydro-furan-2-yloxy)-5-(2-(4,6,7-trihydroxy-hexahydro-benzo(1,3)dioxol-5-ylcarbamoyl)-propenyl)-phenyl) ester;

Phosphoric acid mono-(2-(5-(1-(3-chloro-4-fluoro-benzyloxy-E-imino)-ethyl)-3,4-dihydroxy-tetrahydro-furan-2-yloxy)-5-(2-(4,6,7-trihydroxy-hexahydro-benzo(1,3)dioxol-5-ylcarbamoyl)-propenyl)-phenyl) ester;

Phosphoric acid mono-(2-(5-(1-(3-chloro-benzyloxy-E-imino)-ethyl)-4-hydroxy-tetrahydro-furan-2-yloxy)-5-(2-(4,6,7-trihydroxy-hexahydro-benzo(1,3)dioxol-5-ylcarbamoyl)-propenyl)-phenyl) ester;

Phosphoric acid mono-(2-(5-(1-(3-fluoro-benzyloxy-E-imino)-ethyl)-4-hydroxy-tetrahydro-furan-2-yloxy)-5-(2-(4,6,7-trihydroxy-hexahydro-benzo(1,3)dioxol-5-ylcarbamoyl)-propenyl)-phenyl) ester;

Phosphoric acid mono-(2-(5-(3-(2-chloro-4-fluoro-phenoxy)-1-methyl-propenyl)-3,4-dihydroxy-tetrahydrofuran-2-yloxy)-5-(2-(4,6,7-trihydroxy-hexahydro-benzo(1,3)dioxol-5-ylcarbamoyl)-propenyl)-phenyl) ester; and Phosphoric acid mono-(2-(5-(3-(2-chloro-4-fluoro-phenoxy)-1-methyl-propenyl)-4-hydroxytetrahydrofuran-2-yloxy)-5-(2-(4,6,7-trihydroxy-hexahydro-benzo(1,3)dioxol-5-ylcarbamoyl)-propenyl)-phenyl) ester.

The invention also relates to a method of preparing a compound of formula I as defined above, which comprises treating a compound of formula II (see, e.g., Scheme 1) in the presence of about 1 equivalent of base, with an agent comprising about 1 equivalent of an anhydride or an acylating agent of the formula $R^9C(O)L$ or a phosphorylating agent of the formula $((R^4O)_2PO)_2O$, $(R^4O)_2P(O)Cl$, or $(R^4O)_2P(O)Br$ or a sulfonating agent of the $(R^4O)S(O)_2Cl$ or $(R^4O)S(O)_3$ or an amino acylating agent having the formula $R^{10}R^7N(CHR^5)C(O)Cl$ or $R^{10}R^7N(CHR^5)C(O)Br$; wherein $R^9$ is hydrogen, $(C_1-C_6)$alkyl, $(C_6-C_{10})$aryl, $(C_6-C_{10})$aryl $(C_1-C_6)$alkyl, $(C_2-C_9)$heteroaryl, $(C_2-C_9)$heteroaryl $(C_1-C_6)$alkyl, $(C_2-C_9)$heterocycloalkyl, $(C_2-C_9)$heterocycloalkyl$(C_1-C_6)$alkyl, $R^6$pyridinium$(C_1-C_6)$alkyl or $(R^8)_3N^+(C_1-C_6)$alkyl; wherein $R^{10}$ is a suitable protecting group; wherein L is chloro, bromo or imidazole; provided that sulfonation with $(R^4O)S(O)_2Cl$ or $(R^4O)S(O)_3$ is followed by hydrolysis to yield the compound of formula I; and provided that following treatment with an amino acylating agent, $R^{10}$ is removed to provide the compound of formula I. In an embodiment, $R^{10}$ is carbobenzyloxy or tert-butoxycarbonyl.

The invention also relates to a pharmaceutical composition for the treatment of a disorder selected from a bacterial infection, a protozoal infection, and disorders related to bacterial infections or protozoal infections, in a mammal, fish, or bird which comprises a therapeutically effective amount of a compound of formula I, or a pharmaceutically acceptable salt thereof, and a pharmaceutically acceptable carrier. In an embodiment thereof, the composition comprises a compound of formula I wherein Y is nitrogen, a is zero, Z is oxygen and b is one. In another embodiment thereof, the composition comprises a compound of formula I wherein Y is CH, a is one, Z is oxygen and b is zero. In still further embodiments thereof, the composition comprises any one of the preferred compounds of formula I. In yet another embodiment, the composition comprises at least one of the specific preferred compounds of formula I as set forth above. In another embodiment, the composition further comprises another antibiotic. Examples of suitable other antibiotics include, but are not limited to, beta-lactams, vancomycin, aminoglycosides, quinolones, chloramphenicol, tetracyclines and macrolides.

The invention also relates to a method of treating a disorder selected from a bacterial infection, a protozoal infection, and disorders related to bacterial infections or protozoal infections, in a mammal, fish, or bird which comprises administering to said mammal, fish or bird a therapeutically effective amount of a compound of formula I or a pharmaceutically acceptable salt thereof. In an embodiment of the method, the compound of formula I comprises the compound wherein Y is nitrogen, a is zero, Z is oxygen and b is one. In another embodiment of the method, the compound of formula I comprises the compound wherein Y is CH, a is one, Z is oxygen and b is zero. In still further embodiments of the method, the compound comprises any one of the preferred compounds of formula I. In yet another embodiment of the method, the compound comprises at least one of the specific preferred compounds of formula I as set forth above.

The invention also relates to a method of treating a disorder selected from a bacterial infection, a protozoal infection, and disorders related to bacterial infections or protozoal infections, in a mammal, fish, or bird which comprises administering to the mammal, fish or bird a combination comprising a compound of formula I and another antibiotic, wherein the amounts of the compound and of the other antibiotic are together therapeutically effective in treating the disorder. In further embodiments, the compound of the invention may administered prior to, with or after the other antibiotic. Examples of suitable other antibiotics include, but are not limited to, beta-lactams, vancomycin, aminoglycosides, quinolones, chloramphenicol, tetracyclines and macrolides.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus aureus*, coagulase-negative staphylococcal species, or Enterococcus spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Heicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by Cryptosporidium spp.;

odontogenic infection related to infection by viridans streptococci; persistent cough related to infection by *Bordetella pertussis*; gas gangrene related to infection by *Clostridium perfringens* or Bacteroides spp.; and atherosclerosis or cardiovascular disease related to infection by *Helicobacter pylori* or *Chlamydia pneumoniae*.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. In this regard, the invention includes both the E and Z isomers or configurations.

In particular, in this application a wavy bond symbol

⋯⫯⫯⫯⫯ emanating from an sp² hybridized C or N (Y of formula I) designates a single bond in either the Z and E configuration relative to the highest priority substituent of the adjacent sp² hybridized C atom, i.e., relative to the furanyl ring. The compounds of formula I may also exist as tautomers. This invention relates to the use of all such tautomers and mixtures thereof.

The subject invention also includes isotopically-labelled compounds, and the pharmaceutically acceptable salts thereof, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

DETAILED DESCRIPTION OF THE INVENTION

The following reaction Schemes illustrate the preparation of the compounds of the present invention. Unless otherwise indicated a, b, X, Y, Z, $R^1$, $R^2$, $R^3$, $R^4$ in the reaction Schemes and the discussion that follow are defined as above.

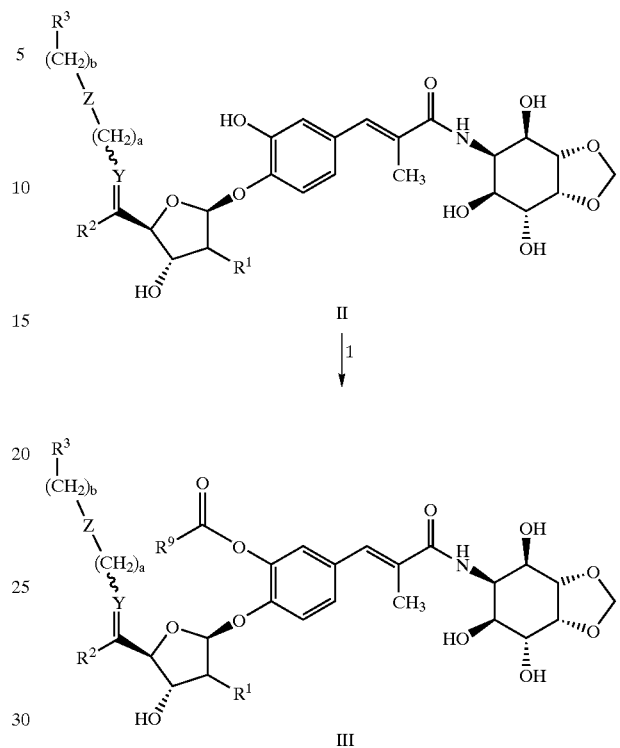

Scheme 1

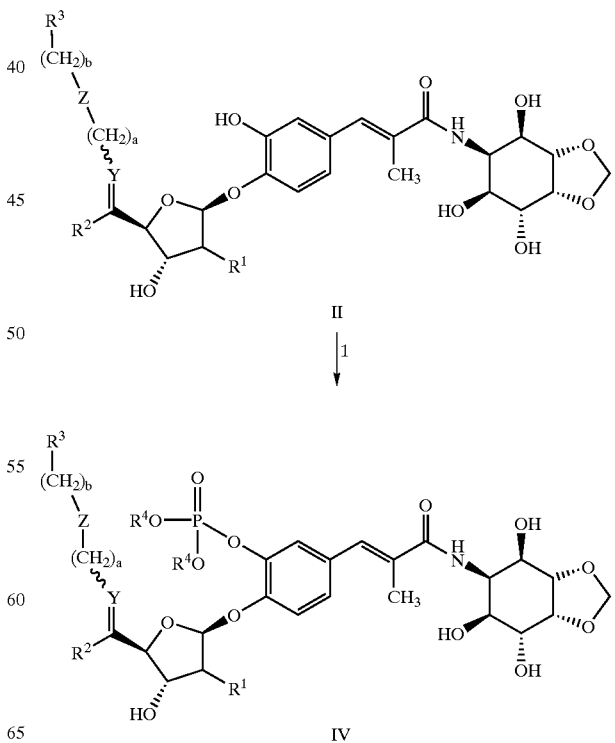

SCHEME 2

SCHEME 3

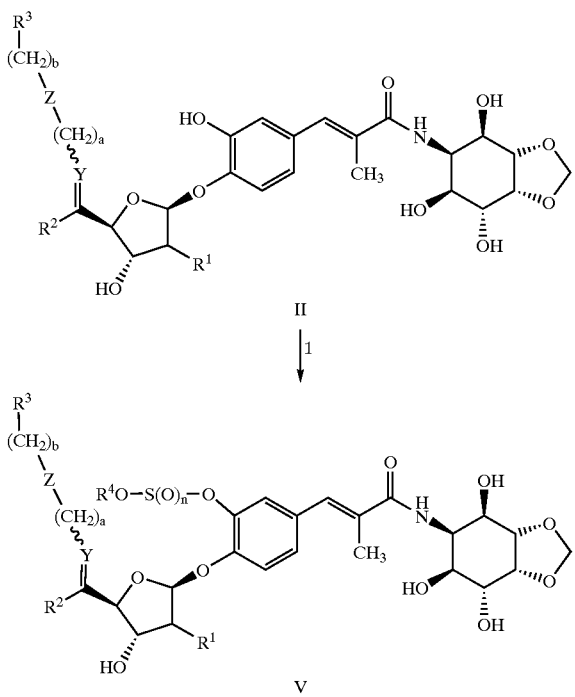

SCHEME 4

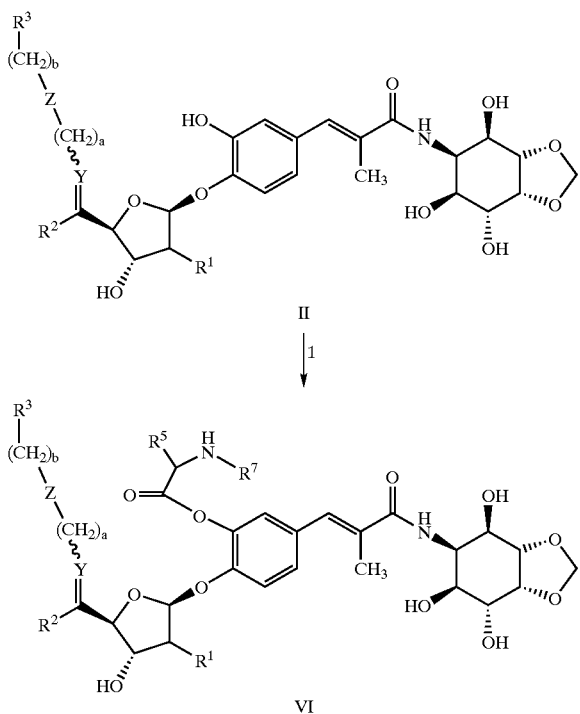

In reaction 1 of Scheme 1, the compound of formula II is converted to the corresponding compound of formula III by reacting II, in the presence of about 1 equivalent of base, such as sodium hydride or potassium hydride, with either 1 equivalent or slightly more than 1 equivalent of (a) an anhydride compound of the formula, $(R^9C(O))_2O$, or (b) an acylating agent of the formula, $R^9C(O)L$, wherein $R^9$ is hydrogen, $(C_1–C_6)$alkyl, $(C_6–C_{10})$aryl, $(C_6–C_{10})$aryl$(C_1–C_6)$alkyl, $(C_2–C_9)$heteroaryl, $(C_2–C_9)$heteroaryl$(C_1–C_6)$alkyl, $(C_2–C_9)$heterocycloalkyl, $(C_2–C_9)$heterocycloalkyl$(C_1–C_6)$alkyl, $R^6$pyridinium$(C_1–C_6)$alkyl or $(R^8)_3N^+(C_1–C_6)$alkyl; and L is chloro, bromo or imidazole. The reaction is stirred in an aprotic solvent, such as tetrahydrofuran, at a temperature range between about −20° C. to about 50° C., preferably about −5° C., for a time period between about 30 minutes to about 24 hours, preferably about 2 hours.

In reaction 1 of Scheme 2, the compound of formula II is converted to the corresponding compound of formula IV by reacting II, in the presence of about 1 equivalent of base, such as sodium hydride or potassium hydride, with either one equivalent or slightly more than one equivalent of (a) a compound of the formula, $((R^4O)_2PO)_2O$, or (b) a phosphorylating agent of the formula, $(R^4O)_2P(O)L$, wherein L is chloro or bromo. The reaction is stirred in an aprotic solvent, such as tetrahydrofuran, at a temperature range between about −20° C. to about 50° C., preferably about 18° C., for a time period between about 30 minutes to about 24 hours, preferably about 2 hours.

In reaction 1 of Scheme 3, the compound of formula II is converted to the corresponding compound of formula V, wherein n is 1, by reacting II, in the presence of about one equivalent of a base, such as sodium hydride or potassium hydride, with one equivalent or slightly more than one equivalent of thionyl chloride. The resulting compound is then treated with a dilute aqueous base (such as $NaHCO_3$). The compound of formula II is converted to the corresponding compound of formula V, wherein n is 2, by reacting II, in the presence of about one equivalent of base, such as sodium hydride or potassium hydride, with either one or slightly more than one equivalent of a sulfuryl chloride or sulfur trioxide, i.e., $(R^4O)SO_2Cl$ or $(R^4O)SO_3$. The intermediate from the sulfuryl chloride is then hydrolyzed by treating with a dilute aqueous base such as $NaHCO_3$. Each reaction is stirred in an aprotic solvent, such as tetrahydrofuran, at a temperature range between about −20° C. to about 50° C., preferably about 0° C., for a time period between about 30 minutes to about 24 hours, preferably about 2 hours, followed by the addition of water or a saturated sodium bicarbonate solution at 0° C. and stirred to an additional time period between about 30 minutes to about 2 hours.

In reaction 1 of Scheme 4, the compound of formula II is converted to the corresponding compound of formula VI by reacting II, in the presence of about one equivalent of a base, such as sodium hydride or potassium hydride, with slightly more than one equivalent of a compound of the formula, $R^{10}R^7N$—$CHR^5$—$C(O)$—L, wherein $R^{10}$ is carbobenzyloxy or tert-butoxycarbonyl and L is chloro, bromo or imidazole. The reaction is stirred in an aprotic solvent, such as tetrahydrofuran, at a temperature range between about −20° C. to about 50° C., preferably about 0° C., for a time period between about 30 minutes to about 24 hours, preferably about 8 hours. Removal of the $R^{10}$ protecting group from the compound so formed to give the corresponding compound of formula VI is carried out under conditions appropriate for that particular $R^{10}$ protecting group in use which will not affect other functional groups. Such conditions include: (a) transfer hydrogenation using 1,4-cyclohexadiene and 10% palladium on carbon under inert atmosphere when $R^{10}$ is carbobenzyloxy or (b) trimethylsilyl, trifluoromethylsulfonate and diisopropylethylamine when $R^{10}$ is tert-butoxycarbonyl.

The compounds of the present invention have asymmetric carbon atoms. Compounds having a mixture of isomers at one or more centers will exist as diastereomeric mixtures, which can be separated into their individual diastereomers on the basis of their physical chemical differences by methods known to those skilled in the art, for example, by chromatography or fractional crystallization. All such isomers, including diastereomer mixtures, are considered as part of the invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case, stoichiometric quantities of reagents are preferably employed in order to ensure completeness of reaction and maximum yields of the desired final product.

The antibacterial activity of the compounds of the present invention against bacterial pathogens is demonstrated by the compound's ability to inhibit growth of defined strains of pathogens.

Assay

The assay, described below, employs conventional methodology and interpretation criteria and is designed to provide direction for chemical modifications that may lead to compounds with antibacterial activity against susceptible and drug-resistant organisms including, but not limited to, beta-lactam, macrolide and vancomycin resistance. In the assay, a panel of bacterial strains is assembled to include a variety of target pathogenic species, including representatives of antibiotic resistant bacteria. Use of this panel enables the chemical structure/activity relationship to be determined with respect to potency and spectrum of activity. The assay is performed in microtiter trays and interpreted according to *Performance Standards for Antimicrobial Disk SusceDtibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as stock solutions. The compound of Example 1 exhibits antibacterial activity in the microtiter assay described above.

The activity of the compounds of the present invention also may be assessed in accord with Steers replicator technique which is a standard in vitro bacterial testing method described by Steers et al., *Antibiotics and Chemotherapy* 1959, 9, 307.

The in vivo activity of the compounds of the present invention can be determined by conventional animal protection studies well known to those skilled in the art, usually carried out in rodents. According to one in vivo model, compounds are evaluated for efficacy in mouse models of acute bacterial infection. An example of one such in vivo system is provided as follows. Mice (CF1 mixed sex mice; 18–20 g) are allotted to cages upon their arrival, and allowed to acclimate 1–2 days before being placed in a study. The acute infection is produced by intraperitoneal inoculation of bacteria (*Staphylococcus aureus* strain 01A1095) suspended in 5% sterile hog gastric mucin. The inoculum is prepared by: growing the culture overnight at 37° C. on blood agar, harvesting the resulting surface growth with sterile brain heart infusion broth, and adjusting this suspension to a turbidity that when diluted 1:10 into 5% sterile hog gastric mucin would produce 100% lethality.

Mice (10 per group) are treated subcutaneously, at 0.5 hour and 4 hours after challenge. Appropriate non-treated (infected but not treated) and positive (vancomycin or minocycline, etc.) controls are included in each study. Percent survival is recorded after a 4-day observation period; the $PD_{50}$ (mg/kg/dose calculated to protect 50% of infected animals) is determined by the probit method.

A similar assay was used to evaluate the compounds of Example 1 and Example 3 in a mouse peritonitis infection model vs. a susceptible strain of *Staphylococcus aureus* (Pfizer designation 01A1146). Mice were challenged intraperitoneally with $1.5 \times 10^5$ cfu (LD100) of *S. aureus* suspended in 10% hog gastric mucin. The compound (100, 50, 25 and 12.5 mg/kg) was given at 0.5 and 4 hrs. post-challenge using a subcutaneous route of drug administration for both the compound (ester) and its precursor hydroxy or "parent" compound. The dosage forms for the compounds were prepared in a 20% β-cyclodextrin or $H_2O$ vehicle and the parent compound was prepared only in 20% β-cyclodextrin. Survivors were recorded over a 5 day period and $PD_{50}$ values were estimated from survival data on day 5 using non-linear regression techniques. The compounds of Example 1 and Example 3 provided protection against the infection in this assay with $PD_{50}$ values within the above dosage range. These examples serve only to illustrate the antibacterial activity of the compounds of the invention, and no limitations are to be inferred from the examples provided.

The compounds of the present invention, and the pharmaceutically acceptable salts thereof (hereinafter "the active compounds"), may be administered through oral, parenteral, topical, or rectal routes in the treatment of bacterial and protozoal infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 3 mg/kg/day to about 60 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous ethanol or propylene glycol may be employed. Use of a cyclodextrin derivative such as β-cyclodextrin sulfobutyl ether, sodium salt (see U.S. Pat. No. 5,134,127) may also be advantageous. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels. Methods of preparing various pharmaceutical compositions with a specific amount of active compound are known, or will be apparent, to those skilled in this art. For examples, see *Remington's Pharmaceutical Sciences*, Mack Publishing Company, Easton, Pa., 18th Edition (1990).

The present invention is further described and exemplified in the preparations and examples described below. In the preparations and examples, "rt" means room or ambient temperature which is a temperature within the range of about 20–25° C.

EXAMPLE 1

2.2-Dimethyl-propionic acid 2-(5-(1-(3-Chloro-benzyloxy-E-imino)-ethyl)-3,4-dihydroxy-tetrahydro-furan-2-yloxy)-5-(2-(4,6,7-trihydroxy-hexahydro-benzo(1, 3)dioxol-5-ylcarbamoyl)-propenyl)-phenyl) Ester To a solution of 3-(4-(5-(1-(3-chloro-benzyloxy-E-imino)-ethyl)-3,4-dihydroxy-tetrahydro-furan-2-yloxy)-3-hydroxy-phenyl)-2-methyl-N-(4,6,7-trihydroxy-hexahydro-benzo(1,3)dioxol-5-yl)-acrylamide (245 mg, 0.376 mmol) in 1.5 mL of tetrahydrofuran was added 21 mg of sodium hydride 60% oil dispersion (0.436 mmol). The mixture was stirred at −5° C. under nitrogen for 10 minutes. Trimethylacetyl chloride (66 μL, 0.527 mmol) was added at −5° C. The solution was stirred at −5° C. for 1.5 hours. The solvent was evaporated and the residue was chromatographed on $SiO_2$ (20% MeOH—$CH_2Cl_2$) to give 151 mg of the title compound; MS m/e 735 (M+).

EXAMPLE 2

Phosphoric Acid dibenzyl-(2-(5-(1-(3-Chloro-benzyloxy-E-imino)-ethyl)-3,4-dihydroxy-tetrahydro-furan-2-yloxy)-5-(2-(4,6,7-trihydroxy-hexahydro-benzo(1.3)dioxol-5-ylcarbamoyl)-propenyl)-phenyl) Ester To a solution of 3-(4-(5-(1-(3-chloro-benzyloxy-E-imino)-ethyl)-3,4-dihydroxy-tetrahydro-furan-2-yloxy)-3- hydroxy-phenyl)-2-methyl-N-(4,6,7-trihydroxy-hexahydro-benzo(1,3)dioxol-5-yl)-acrylamide (100 mg, 0.154 mmol) in 2 mL of tetrahydrofuran was added 8.6 mg of sodium hydride 60% oil dispersion. The solution was stirred at 0° C. for 5 minutes and then tetrabenzyl pyrophosphate (120 mg, 0.215 mmol) was added. The mixture was stirred for 2 hours. Brine was added and the mixture was extracted with ethyl acetate. The organic layer was dried over $Na_2SO_4$ and evaporated. The residue was chromatographed on $SiO_2$ (20% MeOH—$CH_2Cl_2$) to give 52 mg of the title compound; MS m/e 911 (M+).

EXAMPLE 3

Phosphoric Acid Mono-(2-(5-(1-(3-Chloro-benzyloxy-E-imino)-ethyl)-3,4-dihydroxy-tetrahydro-furan-2-yloxy)-5-(2-(4,6,7-trihydroxy-hexahydro-benzo(1,3)dioxol-5-ylcarbamoyl)-propenyl)-phenyl) Ester A solution of phosphoric acid dibenzyl-(2-(5-(1-(3-chloro-benzyloxy-E-imino)-ethyl)-3,4-dihydroxy-tetrahydro-furan-2-yloxy)-5-(2-(4,6,7-trihydroxy-hexahydro-benzo(1,3)dioxol-5-ylcarbamoyl)-propenyl)-phenyl) ester (95 mg, 0.105 mmol) and 168 mg of 1,4-cyclohexadiene (2.1 mmol) and 95 mg 10% palladium on carbon was stirred under nitrogen for 20 hours. The reaction mixture was filtered through Celite and evaporated. The residue was chromatographed on reversed phase $SiO_2$ (30% methanol/water) to give 63 mg of the title compound; MS m/e 731 (M+).

What is claimed is:

1. A compound of the formula

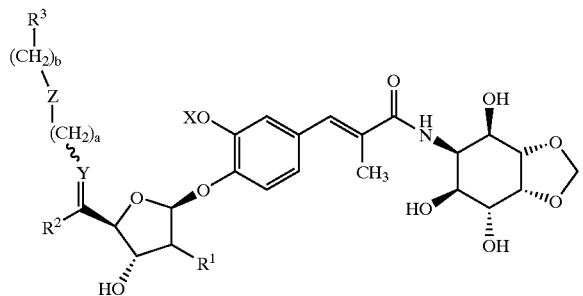

I or a pharmaceutically acceptable salt or solvate thereof; wherein a is 0 or 1;

b is 0, 1, 2 or 3;

$R^1$ is hydrogen or hydroxy;

$R^2$ is methyl;

$R^3$ is $(C_6-C_{10})$aryl optionally substituted by one to three groups independently selected from the group consisting of hydrogen, halo, $(C_1-C_6)$alkoxy, amino, $(C_1-C_6)$alkylamino, $((C_1-C_6)$alkyl$)_2$amino, nitro, $(C_1-C_6)$alkoxy, $(C_1-C_6)$alkoxyC(O), $(C_1-C_6)$alkylaminoC(O), $(C_6-C_{10})$aryl, $(C_2-C_9)$heterocycloalkyl, $(C_2-C_9)$heteroaryl and $(C_1-C_6)$alkyl optionally substituted by one to three fluoro;

X is $(R^4O)_2P(O)$—, $(R^4O)S(O)_n$—, $(C_6-C_{10})$arylC(O), $(C_2-C_9)$heteroarylC(O), $(C_2-C_9)$heterocycloalkylC(O), $(R^7)_2N(CHR^5)C(O)$—, $R^6$pyridinium$(C_1-C_6)$acyl, $(R^8)_3N^+(C_1-C_6)$acyl, $(C_1-C_6)$acyl, $(C_6-C_{10})$aryl$(C_1-C_3)$acyl, $(C_2-C_9)$heteroaryl$(C_1-C_3)$acyl or $C_9)$heterocycloalkyl$(C_1-C_3)$acyl;

wherein n is 1 or 2;

$R^4$ is hydrogen, $(C_1-C_5)$alkyl, $(C_6-C_{10})$aryl or an alkaline metal;

$R^5$ is hydrogen, $(C_1-C_6)$alkyl optionally substituted by hydroxy, aminoC(O)—, thio, methylthio, carboxy or amino; $(C_6-C_{10})$aryl optionally substituted by hydroxy; or $(C_2-C_9)$heteroaryl;

$R^6$ is hydrogen, halo, nitro, amino, $(C_1-C_6)$alkylamino, $((C_1-C_6)$alkyl$)_2$amino, hydroxy, $(C_1-C_6)$alkoxy, $(C_1-C_6)$alkyoxyC(O) or $(C_1-C_6)$alkylaminoC(O);

$R^7$ is hydrogen, $(C_1-C_6)$alkyl, $(C_6-C_{10})$aryl or $(C_6-C_{10})$aryl$(C_1-C_6)$alkyl;

$R^8$ is hydrogen or $(C_1-C_6)$alkyl;

Y is CH or N;

Z is oxygen or $NR^{12}$ wherein $R^{12}$ is hydrogen, $(C_1-C_6)$alkyl or $(C_6-C_{10})$aryl; with the proviso that when Y is CH, a is 1; and with the proviso that when Y is nitrogen, a is zero.

2. A compound according to claim 1, wherein Y is nitrogen, a is zero, Z is oxygen and b is 1.

3. A compound according to claim 2, wherein $R^1$ is hydroxy, X is $(R^4O)_2P(O)$— and $R^4$ is hydrogen or alkaline metal.

4. A compound according to claim 2, wherein $R^1$ is hydroxy and X is $(R^4O)S(O)_n$—, wherein n is 2 and $R^4$ is hydrogen or alkaline metal.

5. A compound according to claim 2, wherein $R^1$ is hydroxy and X is $R^6$pyridinium$(C_1-C_3)$acyl.

6. A compound according to claim 2, wherein $R^1$ is hydrogen, X is $(R^4O)_2P(O)$— and $R^4$ is hydrogen or alkaline metal.

7. A compound according to claim 2, wherein $R^1$ is hydrogen and X is $(R^4O)S(O)_n$—, wherein n is 2 and $R^4$ is hydrogen or alkaline metal.

8. A compound according to claim 2, wherein $R^1$ is hydrogen and X is $R^6$pyridinium$(C_1-C_3)$acyl.

9. A compound according to claim 1, wherein Y is CH, a is 1, Z is oxygen and b is zero.

10. A compound according to claim 9, wherein $R^1$ is hydroxy, X is $(R^4O)_2P(O)$— and $R^4$ is hydrogen or alkaline metal.

11. A compound according to claim 9, wherein X is $(R^4O)S(O)_n$—, wherein n is 2 and $R^4$ is hydrogen or alkaline metal.

12. A compound according to claim 9, wherein $R^1$ is hydroxy and X is $R^6$pyridinium$(C_1-C_3)$acyl.

13. A compound according to claim 1, wherein said compound is selected from the group consisting of:

Phosphoric acid mono-(2-(5-(1-(3-chloro-benzyloxy-Z-imino)-ethyl)-3,4-dihydroxy-tetrahydro-furan-2-yloxy)-5-(2-(4,6,7-trihydroxy-hexahydro-benzo(1,3)dioxol-5-ylcarbamoyl)-propenyl)-phenyl)ester;

Phosphoric acid mono-(2-(5-(1-(3-chloro-4-fluoro-benzyloxy-E-imino)-ethyl)-3,4-dihydroxy-tetrahydro-furan-2-yloxy)-5-(2-(4,6,7-trihydroxy-hexahydro-benzo(1,3)dioxol-5-ylcarbamoyl)-propenyl)-phenyl) ester;

Phosphoric acid mono-(2-(5-(1-(3-chloro-benzyloxy-E-imino)-ethyl)-4-hydroxy-tetrahydro-furan-2-yloxy)-5-(2-(4,6,7-trihydroxy-hexahydro-benzo(1,3)dioxol-5-ylcarbamoyl)-propenyl)-phenyl)ester;

Phosphoric acid mono-(2-(5-(1-(3-fluoro-benzyloxy-E-imino)-ethyl)-4-hydroxy-tetrahydro-furan-2-yloxy)-5-(2-(4,6,7-trihydroxy-hexahydro-benzo(1,3)dioxol-5-ylcarbamoyl)-propenyl)-phenyl)ester;

Phosphoric acid mono-(2-(5-(3-(2-chloro-4-fluoro-phenoxy)-1-methyl-propenyl)-3,4-dihydroxy-tetrahydrofuran-2-yloxy)-5-(2-(4,6,7-trihydroxy-hexahydro-benzo(1,3)dioxol-5-ylcarbamoyl)-propenyl)-phenyl)ester; and Phosphoric acid mono-(2-(5-(3-(2-chloro-4-fluoro-phenoxy)-1-methyl-propenyl)-4-hydroxy-tetrahydrofuran-2-yloxy)-5-(2-(4,6,7-trihydroxy-hexahydro-benzo(1,3)dioxol-5-ylcarbamoyl)-propenyl)-phenyl)ester.

14. A pharmaceutical composition for the treatment of a bacterial infection or a protozoal infection in a mammal, fish, or bird which comprises a therapeutically effective amount of a compound of claim 1 and a pharmaceutically acceptable carrier.

15. A method of treating a bacterial infection or a protozoal infection in a mammal, fish, or bird which comprises administering to said mammal, fish or bird a therapeutically effective amount of a compound of claim 1.

16. A method of preparing a compound of the formula I

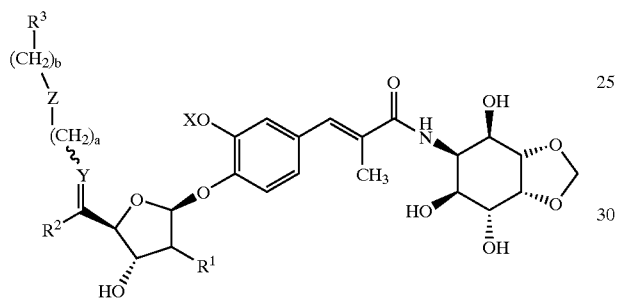

I or a pharmaceutically acceptable salt or solvate thereof, wherein:

a is 0 or 1;

b is 0, 1, 2 or 3;

$R^1$ is hydrogen or hydroxy;

$R^2$ is methyl;

$R^3$ is $(C_6-C_{10})$aryl optionally substituted by one to three groups independently selected from the group consisting of hydrogen, halo, $(C_1-C_6)$alkoxy, amino, $(C_1-C_6)$alkylamino, $((C_1-C_6)$alkyl$)_2$amino, nitro, $(C_1-C_6)$alkoxy, $(C_1-C_6)$alkoxyC(O), $(C_1-C_6)$alkylaminoC(O), $(C_6-C_{10})$aryl, $(C_2-C_9)$heterocycloalkyl, $(C_2-C_9)$heteroaryl and $(C_1-C_6)$alkyl optionally substituted by one to three fluoro;

X is $(R^4O)_2P(O)-$, $(R^4O)S(O)_n-$, $(C_6-C_{10})$arylC(O), $(C_2-C_9)$heteroarylC(O), $(C2-C_9)$heterocycloalkylC(O), $(R^7)_2N(CHR^5)C(O)-$, $R^6$pyridinium$(C_1-C_6)$acyl, $(R^8)_3N^+(C_1-C_6)$acyl, $(C_1-C_6)$acyl, $(C_6-C_{10})$aryl$(C_1-C_3)$acyl, $(C_2-C_9)$heteroaryl$(C_1-C_3)$acyl or $(C2-C_9)$heterocycloalkyl$(C_1-C_3)$acyl; wherein n is 1 or 2;

$R^4$ is hydrogen, $(C_1-C_5)$alkyl, $(C_6-C_{10})$aryl or an alkaline metal;

$R^5$ is hydrogen, $(C_1-C_6)$alkyl optionally substituted by hydroxy, aminoC(O)—, thio, methylthio, carboxy or amino; $(C_6-C_{10})$aryl optionally substituted by hydroxy; or $(C_2-C_9)$heteroaryl;

$R^6$ is hydrogen, halo, nitro, amino, $(C_1-C_6)$alkylamino, $((C_1-C_6)$alkyl$)_2$amino, $(C_1-C_6)$alkoxy, $(C_1-C_6)$alkyoxyC(O) or $(C_1-C_6)$alkylaminoC(O);

$R^7$ is hydrogen, $(C_1-C_6)$alkyl, $(C_6-C_{10})$aryl or $(C_6-C_{10})$aryl$(C_1-C_6)$alkyl;

$R^8$ is hydrogen or $(C_1-C_6)$alkyl;

Y is CH or N;

Z is oxygen or $NR^{12}$ wherein $R^{12}$ is hydrogen, $(C_1-C_6)$alkyl or $(C_6-C_{10})$aryl; with the proviso that when Y is CH, a is 1; and with the proviso that when Y is nitrogen, a is zero;

which comprises treating a compound of formula II

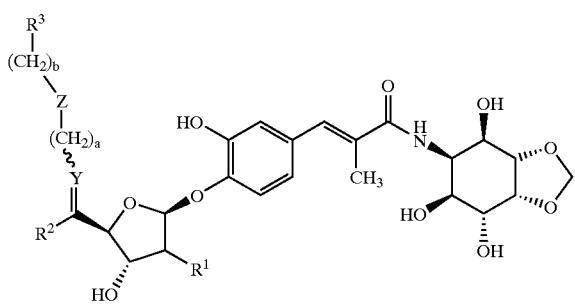

II in the presence of about 1 equivalent of base, with an agent comprising about 1 equivalent of an anhydride or an acylating agent of the formula $R^9C(O)L$ or a phosphorylating agent of the formula $((R^4O)_2PO)_2O$, $(R^4O)_2P(O)Cl$, or $(R^4O)_2P(O)Br$ or a sulfonating agent of the formula $(R^4O)S(O)_2Cl$ or $(R^4O)S(O)_3$ or an amino acylating agent having the formula $R^{10}R^7N(CHR^5)C(O)Cl$ or $R^{10}R^7N(CHR^5)C(O)Br$;

wherein $R^9$ is hydrogen, $(C_1-C_6)$alkyl, $(C_6-C_{10})$aryl, $(C_6-C_{10})$aryl$(C_1-C_6)$alkyl, $(C_2-C_9)$heteroaryl, $(C_2-C_9)$heteroaryl$(C_1-C_6)$alkyl, $(C_2-C_9)$heterocycloalkyl, $(C_2-C_9)$heterocycloalkyl$(C_1-C_6)$alkyl, $R^6$pyridinium$(C_1-C_6)$alkyl or $(R^8)_3N^+(C_1-C_6)$alkyl;

wherein $R^{10}$ is a suitable protecting group;

wherein L is chloro, bromo or imidazole;

provided that sulfonation with $(R^4O)S(O)_2Cl$ or $(R^4O)S(O)_3$ is followed by hydrolysis to yield the compound of formula I; and provided that following treatment with an amino acylating agent, $R^{10}$ is removed to provide the compound of formula I.

* * * * *